United States Patent [19]

Manilla

[11] 4,053,586

[45] Oct. 11, 1977

[54] PREPARATION FOR TREATING SQUAMOUS CELL CARCINOMA AND METHOD FOR MAKING SAME

[75] Inventor: George T. Manilla, Elko, Nev.

[73] Assignee: Intermountain Laboratories, Inc., Salt Lake City, Utah

[21] Appl. No.: 737,549

[22] Filed: Nov. 1, 1976

Related U.S. Application Data

[63] Continuation-in-part of Ser. No. 187,866, Oct. 8, 1971, abandoned.

[51] Int. Cl.$^2$ .................... A61K 35/12; A61K 35/44
[52] U.S. Cl. ........................................... 424/95
[58] Field of Search .......................... 424/95

[56] References Cited

U.S. PATENT DOCUMENTS 3,297,533   1/1967   Szent-Gyorgyi ............... 424/95

OTHER PUBLICATIONS

Merck Veterinary Manual–3rd. Edit. (1967) pp. 649–650.

Primary Examiner—Sam Rosen
Attorney, Agent, or Firm—K. S. Cornaby

[57] ABSTRACT

A biological preparation, method of preparation, and method of treatment of animals as concerns squamous cell carcinoma, known commonly as "Cancer Eye". Used in the preparation of the biological product is tumorous tissue, or culture thereof, obtained from a so-diseased animal. The tumor is introduced into and homogenized in a hypertonic metallic salt solution containing both an adsorbing agent and also a suspending agent. Temperature of the material must not rise during homogenization above 60° C. The homogenized tumor tissue mixture is allowed to stand, with occasional mixing preferred. Certain additives produce useful material which is suitably processed and introduced into an injection medium.

11 Claims, No Drawings

PREPARATION FOR TREATING SQUAMOUS CELL CARCINOMA AND METHOD FOR MAKING SAME

This application is a continuation-in-part application of patent application Ser. No. 187,866, filed Oct. 8, 1971 now abandoned.

The present invention relates to biological preparations and, more particularly, to a new and improved biological preparation, method of preparation, and method of treatment of animals, as concerns squamous cell or epidermoid carcinoma, known to the layman or cattleman as "Cancer Eye".

Authorities indicate that 0.2 percent of all cattle slaughtered in the United States at federally inspected meat packing plants are afflicted with "Cancer Eye". Higher incidences of malignancies are to be expected in non-federally inspected plants. Approximately 7,000 carcasses per year are condemned due to this malignancy. Further, the significance and frequency of occurence of this disease are increased in aged animals.

In the present invention, squamous cell tumorous tissue is taken from a part of the body of a so afflicted animal, and the tissue is used, either directly or via the production of a tissue culture, to provide cancerous cells for introduction and processing in a particular medium. While the tumorous tissue can be taken from any afflicted part of the body, the same can generally be easily found at and readily available from squamous cell tumorous tissue found at the corneal, conjunctival, scleral, palpebra, or nicitating membrane portions of the eye and surrounding structures.

It has been found in the present invention that by properly caring for the tissue and mixing with the same certain chemicals and substances, as hereinafter set forth, a biological preparation may be obtained. The biological preparation in tests has proven very satisfactory for reinjection into the same afflicted animal from which the tumor was taken, or in similarly affected animals. Tests have indicated an actual regression of tumors and other evidences of diminution of the disease, so that many animals can be saved.

By virtue of the regression heretofore observed, as above mentioned, it is believed that the subject biological preparation is also useable advantageously in connection with the immunization of cattle relative to Cancer Eye.

Accordingly, the principal object of the present invention is to provide a biological preparation to be used as a treatment for animals infected with squamous cell carcinoma, known generally as Cancer Eye.

A further object of the invention is to provide a new and improved method of making biological preparation which is suitable to be used in connection with squamous cell carcinoma.

An additional object is to provide a method for treating animals, such as cattle, afflicted with squamous cell carcinoma.

A further object of the invention is to provide a biological preparation, method of preparation, and method of treatment, to combat the cattle disease known as squamous cell carcinoma, whether by treatment of animals with the disease or immunization against the disease.

The features of the present invention together with further objects and advantages thereof may best be understood with reference to the detailed description which follows, takin in connection with the claims appended thereto.

The subject biological preparation is described and may be prepared as follows:

Squamous carcinoma cells are first obtained either from a tissue culture of squamous carcinoma or by direct removal of such tissue from an infected animal. As to tissue removal, the same may take the form of a block resection, with an enucleation procedure, or as tumor slice, and so forth. The resultant selected tumor tissue is now washed free of any clotted blood, dirt, or other debris and, subsequent to washing, is effectively ground as during homogenization, using conventional equipment, in an environment of from 100 to 1000 ml of hypertonic, metallic salt solution per 10 to 100 grams of selected tumor tissue. By hypertonic salt solution is meant a 1 to 5 molar solution of a class of metallic chloride salts comprising, for example, any one of the following salts: $NaCl$, $K\,Cl$, $LiCl$, $ZnCl_2$, $MgCl_2$ and $MnCl_2$.

Consider thus the formation of such a tissue-including hypertonic salt solution of one liter. To such a solution will be added from 0.1 to 10.0 grams of an absorbing agent such as any one of the following: barium sulphate, barium chloride, bentonite, kaolin, aluminum hydroxide, magnesium phosphate, and magnesium pyrophosphate.

Additionally added to such one liter solution will be a suspending agent of from .001 to 1.0%. Thus, additionally added to the tissue-including hypertonic salt solution will be an amount, varying from 0.01 of a gram to 10.0 grams, of one of the following suspending agents: poly vinyl pyrrolidone, sodium desoxycholate, sodium lauryl sulfate, or existing preparations going under the trade marks Triton X, Tween 20, 40, 60, or 80.

In lieu of adding separate adsorption and suspension agents, a combination solution known in the trade under the trademark "Barotrast", (barium sulfate, carboxymethylcellulose, bentonite and sodium saccharin) and including both absorption and suspension agents, may be used.

During homogenization, as above referred to, it is important that the temperature rise of the solution is monitored periodically to keep the temperature of the same at least below 60° C, and preferably below 50° C., so that nucleic acids or proteins as may form will not be altered or destroyed.

Next, the homogenized tumor tissue solution is then placed at 26° C to 37° C temperature and allowed to stand and to remain at such temperature range for from twelve to ninety-six hours, with occasional mixing, this to allow for an extraction of the active material. Best results are obtained where the mixture is maintained at said temperature for approximately 72 hours.

Following this time the mixture is then centrifuged for approximately 15 minutes at 2000 rpm. The purpose for the centrifuging action is to eliminate from the recovered supernatant extraneous unwanted matter or dross.

Following the centrifuging of the mixture, the following are combined with the supernatant in the relative volumetric amounts indicated:

1. One volume of the supernatant from the centrifuged mixture;
2. One-fourth volume of an aqueous, metallic salt solution, e.g. 10% agueous, metallic salt solution (calcium chloride, magnesium chloride, manganese chloride, lithium chloride or zinc chloride);

3. One and one-fourth volumes of an alcohol, i.e. methyl alcohol or ethyl alcohol;

to make a total volumetric solution of two and one-half volumes.

The resultant mixture is placed at from 4° C to 25° C for approximately 12 hours, this to derive a precipitate including the so-processed reduced tissue or tissue cells. The resultant precipitate is then dissolved in an extracting medium as in from 100 to 400 cc of aqueous phenol (80 gram crystal phenol and 20 ml water) and the mixture placed at from 20° C to 37° C from 24 to 96 hours. This last mixture is again centrifuged and the phenol-soluble fraction dialyzed against cold tap water (12° C to 15° C) until mostly free of phenol. The resultant red, chunky material is then ground in sterile water or saline prior to use by syringe injection.

As a slight modification of the above preparation, it should be noted that, following precipitation, the precipitate may be further extracted by use of an alternative extracting medium, an ether-ethyl alcohol preparation maintained at boiling and hence evaporation point (34.6° C), this to yield an active preparation.

Accordingly, the method of making a biological preparation, as concerns squamous cell carcinoma, for injection into animals comprises the following steps:

Providing squamous carcinoma cells; homogenizing said cells in a hypertonic salt solution containing an adsorbing agent and a suspending agent in manner such that, during homogenization, the temperature thereof does not exceed 60° C; permitting said mixture to stand at least 24 hours between 26° C and 37° C; centrifuging said mixture to produce a supernatant; recovering said supernatant; adding to said supernatant an alcohol and a metallic salt; placing the resulting mixture from the next preceding step in an environment at a temperature of 4° C to 25° C and allowing the same to stand for a minimum of 12 hours, to derive a precipitate; dissolving said precipitate in an extracting medium; reducing the presence of said extracting medium to provide useable material; reducing the particulate size of said useable material in the next preceding step; and mixing the so-reduced material with a diluent to constitute an injectable solution.

The biological preparation itself, as concerns squamous cell carcinoma for injection in animals, comprises a ground precipitate dispersed in a fluid medium, said particulate matter being derived through the following method of preparation:

Providing squamous carcinoma cells, homogenizing said cells in a hypertonic salt solution containing an adsorbing agent and a suspending agent in a manner such that, during homogenization, the temperature thereof does not exceed 60° C; permitting said mixture to stand at least 24 hours between 26° C and 37° C; centrifuging said mixture to produce a supernatant; recovering said supernatant; adding to said supernatant an alcohol and a metallic salt; placing the resulting mixture from the next preceding step in an environment at a temperature of 4° C to 25° C and allowing the same to stand for a minimum of 12 hours, to derive a precipitate; dissolving said precipitate in an extracting medium; reducing the presence of said extracting medium to provide useable material; reducing the particulate size of said useable material in the next preceding step; and mixing the so-reduced material with a diluent to constitute an injectable solution.

An injectable solution for a single intramuscular or subcutaneous injection can be made by suspending from 60 mg. to 240 mg. of dried material in 2-10 ml. of saline or sterile water per 1000 lbs. body weight of the animal and be injected. Such dosage is effective in causing regression of up to 70% of ocular squamous cell carcinoma lesions of size 2 cm. in diameter or smaller. This dosage can be applied to larger lesions, but the efficacy is ratably diminished.

Finally, the method of the present invention as concerns the treatment of cattle afflicted when squamous cell carcinoma comprises the following steps:

Obtaining from afflicted animal squamous cell carcinoma tissue; processing said tissue to provide squamous carcinoma cells; homogenizing said cells in a hypertonic salt solution containing an adsorbing agent and a suspending agent in a manner such that, during homogenization, the temperature thereof does not exceed 60° C; permitting said mixture to stand at least 24 hours at 26° C to 37° C; centrifuging said mixture to produce a supernatant; recovering said supernatant; adding to said supernatant an alcohol and a metallic salt; placing the resulting mixture from the next preceding step in an environment at a temperature of 4° C to 25° C and allowing the same to stand for a minimum of 12 hours; to derive a precipitate; dissolving said precipitate in an extracting medium; reducing the presence of said extracting medium to provide useable materials; reducing the particulate size of said useable material in the next preceding step; mixing the so-reduced material with a diluent to constitute an injectable solution; and injecting said injectionable solution in afflicted animals.

As to packaging, supply vials are filled as by using an electric dispenser with a roller pump. Vials may be single or multiple dose ampules which are stopped with rubber flange stoppers and sealed with aluminum seals in a conventional manner.

While particular embodiments of the present invention have been described, it will be obvious to those skilled in the art that changes and modifications may be made without departing from this invention in its broader aspects, and, therefore, the aim in the appended claims is to cover all such changes and modifications as fall within the true spirit and scope of this invention.

I claim:

1. A method for preparing a biological preparation for treatment of squamous cell carcinoma, comprising the steps of:

homogenizing squamous cell carcinoma cells in a one to five molar hypertonic metallic chloride salt solution containing an adsorbing agent and a suspending agent at a temperature below about 60° C.;

extracting the cells in the suspension for at least about 12 hours at a temperature of at least about 26° C.;

separating the liquid extract from the solid material to produce a liquid containing the cell extract;

contacting the liquid containing the cell extract with an aqueous metallic chloride salt solution and a low carbon chain alcohol for at least about 12 hours at a temperature of from about 4° C to about 25° C to to strip the cell extract from the liquid and to form a precipitate containing the extract;

dissolving the precipitate in an organic extraction medium, and allowing the solution to stand for a sufficient amount of time to purify the extract; and reducing the presence of the extracting medium to precipitate the purified cell extract.

2. A method as set forth in claim 1, wherein the first extraction takes place for a period of up to about 96 hours at a temperature of up to about 37° C.

3. A method as set forth in claim 1, wherein the metallic chloride salt contained in the aqueous metallic chloride salt solution is selected from the group consisting of calcium chloride, magnesium chloride, manganese chloride, lithium chloride and zinc chloride; and the low chain alcohol is selected from the group consisting of methyl, ethyl and isopropyl alcohols.

4. A method as set forth in claim 1, wherein the organic extracting medium is selected from the group consisting of phenol and an ether-ethyl alcohol mixture.

5. A method as set forth in claim 1, wherein the purified cell extract is solubilized in water for injection into animals.

6. The method of claim 1, wherein, in said homogenizing step said hypertonic metallic salt solution comprises an aqueous solution having at least one metallic salt of the following class of metallic salts; sodium chloride, potassium chloride, lithium chloride, calcium chloride, magnesium chloride, and manganese chloride.

7. The method of claim 1, wherein, in said homogenizing step, said adsorbing agent comprises one of the following class: barium sulphate, bentonite, kaolin, aluminum hydroxide, magnesium phosphate, and magnesium pyrophosphate.

8. The method of claim 1, wherein, in said homogenizing step, said suspending agent comprises one of the following class of suspending agents: poly vinyl pyrollidone, sodium desoxycholate, sodium lauryl sulfate, Triton X, Tween 20, Tween 40, Tween 60 or Tween 80.

9. The method of claim 1, wherein, in said homogenizing step, said hypertonic salt solution contains as a composite of said adsorbing agent and suspending agent comprising barium sulfate, carboxymethylcellulose, bentonite and sodium saccharin.

10. A biological preparation of treatment of squamous cell carcinoma, comprising an extract from squamous cell carcinoma cells prepared by the following steps:
homogenizing squamous cell carcinoma cells in a one to five molar hypertonic metallic chloride salt solution containing an adsorbing agent and a suspending agent at a temperature below about 60° C.;
extracting the cells in the suspension for at least about 12 hours at a temperature of at least about 26° C;
separating the liquid extract from the solid material to produce a liquid containing the cell extract:
contacting the liquid containing the cell extract with an aqueous metallic chloride salt solution and a low carbon chain alcohol for at least about 12 hours at a temperature of from about 4° C to about 25° C to strip the cell extract from the liquid and to form a precipitate containing the extract;
dissolving the precipitate in an organic extraction medium, and allowing the solution to stand for a sufficient amount of time to purify the extract; and
reducing the presence of the extracting medium to precipitate the purified cell extract.

11. A biological preparation as set forth in claim 10, wherein the purified cell extract is suspended in a water solution for injection into an animal.

* * * * *